(12) United States Patent
Nguyen

(10) Patent No.: US 9,763,574 B2
(45) Date of Patent: Sep. 19, 2017

(54) HOOD FOR AN OPHTHALMIC DEVICE

(71) Applicant: Kelvin Nguyen, San Diego, CA (US)

(72) Inventor: Kelvin Nguyen, San Diego, CA (US)

( * ) Notice: Subject to any disclaimer, the term of this patent is extended or adjusted under 35 U.S.C. 154(b) by 89 days.

(21) Appl. No.: 14/859,294

(22) Filed: Sep. 19, 2015

(65) Prior Publication Data
US 2017/0049321 A1    Feb. 23, 2017

Related U.S. Application Data

(63) Continuation-in-part of application No. 29/537,140, filed on Aug. 21, 2015.

(51) Int. Cl.
| | | |
|---|---|---|
| *A61B 3/00* | (2006.01) | |
| *A61B 3/12* | (2006.01) | |
| *A61B 3/14* | (2006.01) | |
| *A61B 3/10* | (2006.01) | |
| *A61B 3/103* | (2006.01) | |
| *A61B 3/028* | (2006.01) | |
| *A61B 3/024* | (2006.01) | |
| *A61B 3/107* | (2006.01) | |
| *A61B 3/16* | (2006.01) | |
| *G03B 11/04* | (2006.01) | |

(52) U.S. Cl.
CPC .............. *A61B 3/12* (2013.01); *A61B 3/0083* (2013.01); *A61B 3/024* (2013.01); *A61B 3/0285* (2013.01); *A61B 3/102* (2013.01); *A61B 3/103* (2013.01); *A61B 3/107* (2013.01); *A61B 3/1015* (2013.01); *A61B 3/14* (2013.01); *A61B 3/16* (2013.01); *G03B 11/048* (2013.01)

(58) Field of Classification Search
CPC .............. A61B 3/14; A61B 3/112; A61B 3/12

USPC ....... 351/239, 245; 359/613; 362/496, 23.13
See application file for complete search history.

(56) References Cited

U.S. PATENT DOCUMENTS

| | | | |
|---|---|---|---|
| 2,952,853 A | 9/1960 | Benzel | |
| 3,255,428 A | 6/1966 | Robbins | |
| 3,763,348 A | 10/1973 | Costello | |
| 5,024,602 A | 6/1991 | Leong | |
| D327,024 S | 6/1992 | Elie | |
| 5,274,501 A * | 12/1993 | Stroll, Jr. ............... | G02B 5/005 348/834 |
| 5,319,732 A | 6/1994 | Jones | |
| 5,694,199 A * | 12/1997 | Rodriguez ............... | A61B 3/06 351/223 |
| D390,663 S | 2/1998 | Wolf | |
| D394,505 S | 5/1998 | Hayashi | |
| 5,906,287 A | 5/1999 | Kohnen | |
| D465,850 S | 11/2002 | Takizawa | |
| 7,568,798 B2 | 8/2009 | Krefman | |
| 8,147,063 B2 | 4/2012 | Krefman | |
| D698,444 S | 1/2014 | Mensink | |
| D705,430 S | 5/2014 | Sekine | |
| 2005/0264760 A1* | 12/2005 | Ikezawa ................ | A61B 3/103 351/239 |
| 2007/0132946 A1 | 6/2007 | Krefman | |
| 2010/0020285 A1 | 1/2010 | Berge | |
| 2013/0100401 A1 | 4/2013 | Tabor | |

* cited by examiner

*Primary Examiner* — Hung Dang
(74) *Attorney, Agent, or Firm* — MDIP LLC

(57) ABSTRACT

The present invention describes a rectangular parabolic hood for blocking accommodation and reducing depth of focus to offset the negative affects of extraneous light and visual stimulus during examination of the pupil using ophthalmic instruments.

20 Claims, 5 Drawing Sheets

HOOD FOR AN OPHTHALMIC DEVICE

CROSS REFERENCE TO RELATED APPLICATION

This application is a continuation-in-part of U.S. Design application No. 29/537,140, filed Aug. 21, 2015, which is incorporated by reference herein in its entirety.

BACKGROUND OF THE INVENTION

Field of the Invention

The present invention relates generally to ophthalmic devices and instruments, and specifically to an opaque parabolic hood for reducing the accommodation response of the pupil during eye examinations, including ophthalmic systems containing said parabolic hood and method of using said parabolic hood to reduce accommodation by the pupil and reduce depth of focus in the eye.

Background Information

The accommodation response is elicited when the viewer directs his/her eyes from a distant (e.g., greater than 30 ft away) object to a nearby object. The stimulus is an "out of focus" image. The accommodation (near point) response is consensual (i.e., it involves the action of the muscles of both eyes).

The accommodation response involves three actions:

Pupil accommodation: during accommodation, pupil constriction uses the "pin hole" effect and increases depth of focus of the eye by blocking the light scattered by the periphery of the cornea.

Lens accommodation: lens accommodation increases the curvature of the lens, which increases its refractive (focusing) power.

Convergence in accommodation: when shifting one's view from a distant object to a nearby object, the eyes converge (are directed nasally) to keep the object's image focuses on the foveae of the two eyes.

The normal pupil size in adults varies from 2 to 4 mm in diameter in bright light to 4 to 8 mm in the dark. The pupils are generally equal in size. They constrict to direct illumination (direct response) and to illumination of the opposite eye (consensual response). The pupil dilates in the dark. When a non-occluded eye is looking straight ahead, it will receive visual stimulus of near objects such as equipment, technician, walls, and the like, which would result in pupil constriction of both pupils (consensual response).

All ophthalmic instruments require light to enter the pupil, and image quality is influenced by pupil size. Many instruments on the market are greatly affected by light and pupil size. However, extraneous light (i.e., light that strikes the eye from above or laterally relative to the subject's head) or visual stimulus of near objects causes accommodation stimulus, which again, results in consensual constriction of both pupils. What is needed is an effective method to block these stimuli, as well as reduce depth of focus.

SUMMARY OF THE INVENTION

The present invention discloses a device for blocking accommodation and reducing depth of focus to offset the negative affects of extraneous light and visual stimulus during examination of the pupil using ophthalmic instruments.

In embodiments, an ophthalmic system is disclosed including an ophthalmic instrument comprising a housing and a light collecting device and a substantially rectangular opaque parabolic hood anchored to one or more outer surfaces of said instrument, where the apex of the parabolic hood is above the housing of the instrument and the base of said parabolic hood runs parallel to the horizontal axis of the housing, where the parabolic hood comprises one or more thin sheets, and where the parabolic hood is configured to cover at least the light collecting device of the instrument and the front of the head of a subject substantially midcranially when the front of the head of the subject is proximal to the light collecting device.

In one aspect, the parabolic hood includes at least two substantially rectangular deflectable plates attached to an inner surface of the parabolic hood, where the top of the deflectable plates is proximal to the beginning of the inner curvature of the arc of the parabolic hood and the bottom of the deflectable plates is parallel to the base of the parabolic hood. In a related aspect, the deflectable plates are configured to substantially oppose each other. In a further related aspect, the deflectable plates are attached to the inner surface of the hood through hinges attached to the base of the parabolic hood distal to the parabolic apex. In another related aspect, the deflectable plates deviate 180° relative to the long axis of the base of the parabolic hood.

In another aspect, the material in the one or more thin sheets includes a polymer, metal, composite or combination thereof.

In one aspect, the ophthalmic instrument includes a retinal camera, an aberrometer, an ophthalmoscope, an imaging system, a fundus camera, a refraction system, a manual refractor, a reflectometer, a wavefront system, a tomographer, a slit-lamp system, a phoroptor, a perimeter, a keratometer, head-anchored binoculars, a tonometer, an autorefractor, and an optical coherence tomographer.

In another aspect, the parabolic hood is releasably anchored to the one or more surfaces of the ophthalmic instrument. In a related aspect, parabolic hood is releasably anchored by a one or more clamps.

In one aspect, the one or more surfaces include the top, bottom or side surfaces of the housing, the arms of a head rest, the arms of a chin rest or a combination thereof.

In embodiments, a substantially rectangular opaque parabolic hood is disclosed including one or more thin sheets including materials from a polymer, metal, composite or combination thereof and at least two substantially rectangular deflectable plates attached to an inner surface of the parabolic hood, where the top of the deflectable plates is proximal to the beginning of the curvature of the arc of the parabolic hood and the bottom of the deflectable plates is parallel to the base of the parabolic hood.

In one aspect, the deflectable plates are configured to substantially oppose each other. In a related aspect, the deflectable plates are attached to the inner surface of the hood through hinges connected to the base of the parabolic hood distal to the parabolic apex. In another related aspect, the deflectable plates deviate 180° relative to the long axis of said base of the parabolic hood.

In embodiments, a method of reducing the accommodation response of the pupil during an eye examination using an ophthalmic instrument is disclosed including positioning the head of a subject undergoing examination on a surface of an ophthalmic instrument proximal to a light collecting device of the instrument such that an illumination device contained in the ophthalmic instrument projects light into at least one eye of the subject, where the ophthalmic instrument comprises a substantially rectangular opaque parabolic hood anchored to one or more outer surfaces of the instrument, where the apex of the parabolic hood is above the light collecting device of the instrument, and where the parabolic hood covers the head of the subject substantially mid-cranially, whereby the parabolic hood blocks extraneous light projected above or laterally relative to the head of the subject from entering the at least one eye.

In one aspect, the plates reduce the depth of focus in the at least one eye.

DETAILED DESCRIPTION OF THE INVENTION

Figure 1:
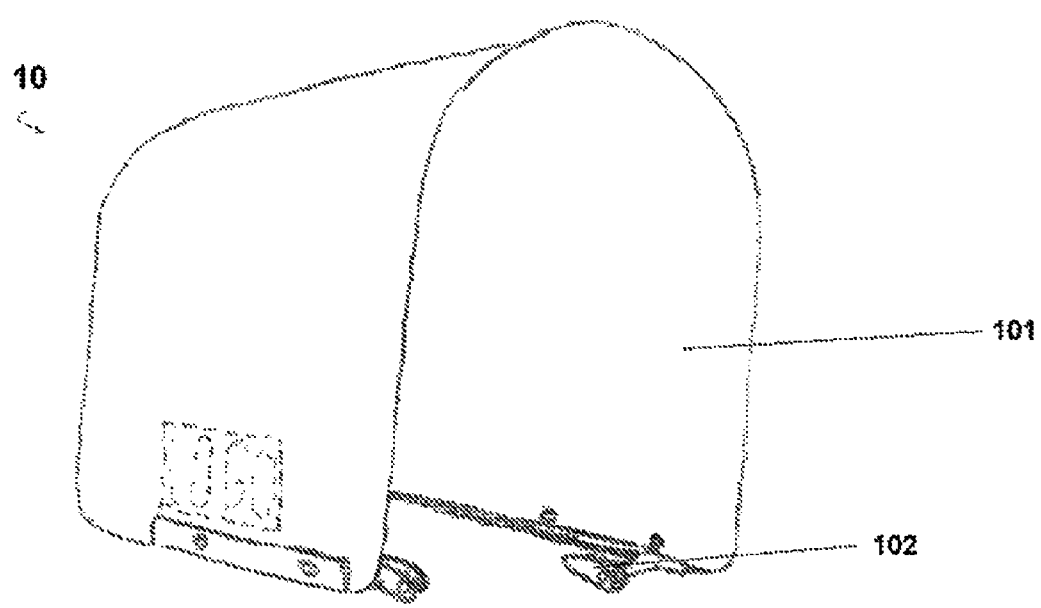
FIG. 1 shows a perspective view of an embodiment of the parabolic hood as disclosed herein.

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a camera" includes one or more cameras, and/or compositions of the type described herein which will become apparent to those persons skilled in the an upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus <10% of particular term. "Substantially" means to a great extent or degree. In embodiments, composition may "contain", "comprise" or "consist essentially of" a particular component of group of components, where the skilled artisan would understand the latter to mean the scope of the claim is limited to the specified materials or steps "and those that do not materially affect the basic and novel characteristic(s)" of the claimed invention.

As used herein "ophthalmic systems" are articles of manufacture that are designed to diagnose and assess vision health, and include, but are not limited to, retinal cameras, aberrometers, ophthalmoscopes, imaging systems, fundus camera, refraction systems, manual refractor, reflectometers, wavefront systems, tomographers, slit-lamp systems, phoroptors, perimeters, keratometers, head-anchored binoculars, tonometers, autorefractors, and optical coherence tomographers.

As used herein, "housing" means a substantially enclosed case and support for a mechanism or article of manufacture.

As used herein, "rectangular" means having right angles or a rectangular base, side, or sides.

As used herein, "parabolic" means a two-dimensional, mirror-symmetrical curve, which is substantially U-shaped when viewed from the front.

As used herein, "anchor" including grammatical variations thereof, means a device, composition or article that serves to hold an object firmly. For example, anchors include, but are not limited to, clips, VELCRO®, screws, glue, fasteners, magnets, collars, nuts, hooks, tabs, straps, clamps, snaps and the like, which would be readily apparent to one of the skill in the art.

As used herein. "hood" means a covering suspended over an object.

As used herein, "releaseably", including grammatical variations thereof, means configured to be freed from physical restraint or binding.

As used herein, "deflectable", including grammatical variations thereof, means capable of being turned aside, bend or deviate. For example, the deflectable plates as described herein may deviate 180° relative to the long axis of the base of the parabolic hood via a hinge.

As used herein, "thin sheet" means a broad, substantially rectangular mass or piece of material relatively small in extent from one surface to the opposite in the smallest solid dimension. In embodiments, the parabolic hood may be made from one or more thin sheets, where the one or more thin sheets may comprise a polymer, a metal, a composite (e.g., wood, concrete, plastic reinforced by glass fibers, and graphite reinforced with carbon fibers and the like as would be apparent to one of skill in the art), or a combination thereof.

As used herein, "opaque" means that the object is neither transparent (allowing all light to pass through) nor translucent (allowing some light to pass through).

Many instruments, such as retinal cameras, are greatly affected by light and pupil size. Pupil constrictions are affected by both light and accommodation. The device of the instant disclosure reduces light and diminishes accommodation. In embodiments, the device comprises a parabolic hood, which when installed on various optical instruments, significantly reduces depth of focus, and thereby reduces accommodation. In a related aspect, by reducing depth of focus in an eye that is occluded, both pupils will dilate fully. In a further related aspect, the parabolic hood may contain two (2) swinging screens that block depth of focus and reduce accommodation, thus, by reducing both light and accommodation stimulus, the pupils may dilate more effectively, allowing more facile and efficacious examination of the eye. The device, and methods of using said device, is described more fully below.

FIG. 1 shows the parabolic hood 10 illustrating an inner surface 101, which may be matte or black, or the inner surface 101 may be modified to absorb light, and a clamping device 102. While a clamping device 102 is shown, any means to anchor the parabolic hood 10 to an available surface may be substituted. For example, such means may include, but are not limited to, clips, VELCRO®, screws, glue, fasteners, magnets, collars, nuts, hooks, tabs, clamps, snaps and the like, which would be readily apparent to one of the skill in the art. Further, surfaces available on the instrument may include, but are not limited to, the top, bottom or side surfaces of the housing, the arms of a head rest, the arms of a chin rest or a combination thereof, as would be apparent to one of the skill in the art. While the anchors 102 as shown are releasable, the hood 10 may be permanently affixed to an ophthalmic instrument, where choice of surface may be left to artisan design.

Figure 2:
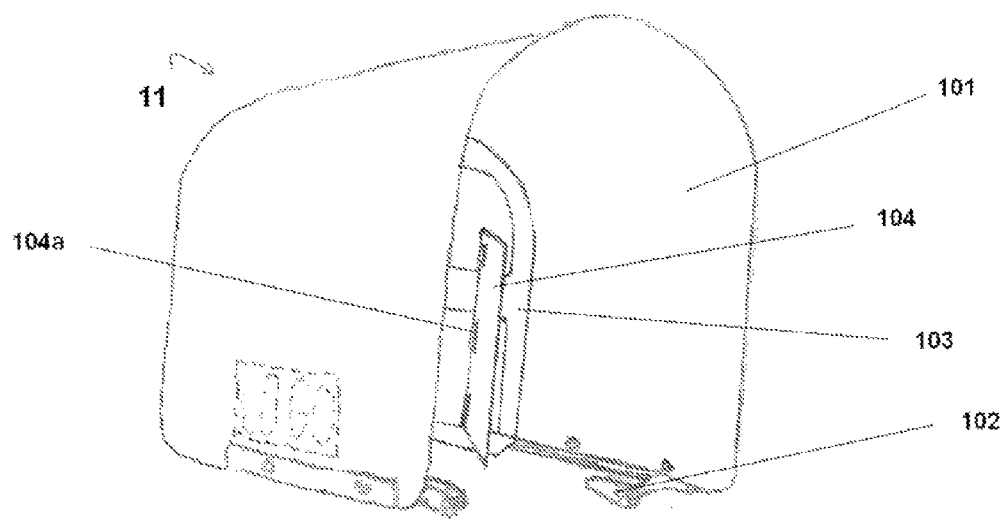
FIG. 2 shows a perspective view of another embodiment of the parabolic hood containing deflector plate as disclosed herein (opposing plate not shown).

FIG. 2 shows another embodiment of parabolic hood 11 illustrating the inner surface 101, brace 103, deflectable plate 104, and clamps 102. The deflectable plates 104 (opposing plate not shown) are attached to the parabolic hood 11 by a brace 103 which connects to a hinge 104a, which is mechanically connected to the plates 104 (although other means to connect the plates to the hood 11 may be used). While plates 104 as shown are deflectable, it will be readily apparent that plates 104 may be custom designed to fit the contours of a housing 105a (refer to FIG. 3), and plate 104 movement may be restricted in design.

Figure 3:
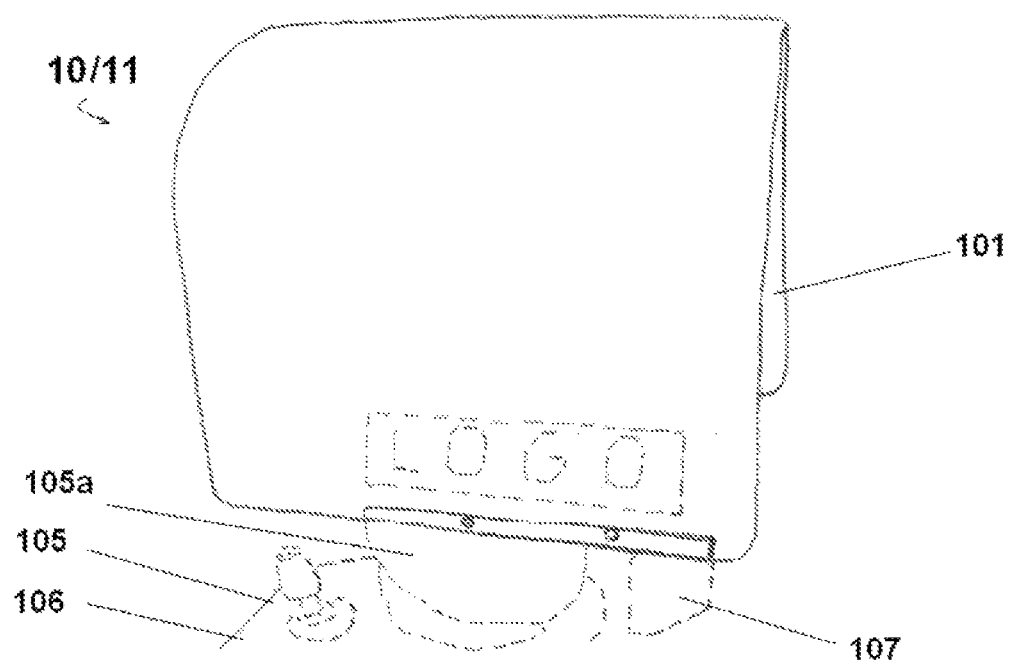
FIG. 3 shows a perspective view of another embodiment of the parabolic hood when anchored to an ophthalmic instrument.

FIG. 3 shows another embodiment of parabolic hood 10/11 illustrating the hood 10/11 mounted on to an ophthalmic instrument 105 (e.g., retinal camera). This embodiment shows that the hood 10/11 covers the housing 10a and chin/head rest 107 of the device 105, where the base of the hood 10/11 runs parallel with base 106 of the instrument 105 (which is more clearly shown in FIGS. 4 and 5). While a retinal camera 105 is shown in FIG. 3, other instruments may be used with the basic hood design, including but not limited to, aberrometers, ophthalmoscopes, imaging systems, fundus camera, refraction systems, manual refractor, reflectometers, wavefront systems, tomographers, slit-lamp systems, phoroptors, perimeters, keratometers, head-anchored binoculars, tonometers, autorefractors, and optical coherence tomographers. Further, while some instruments may not have a base, per se (e.g., head-anchored binoculars), as long as the hood can be attached to the instrument so as to block light from above and lateral to the head of the subject being examined, efficacious positioning of the hood may be achieved in the absence of a true base.

Figure 4:
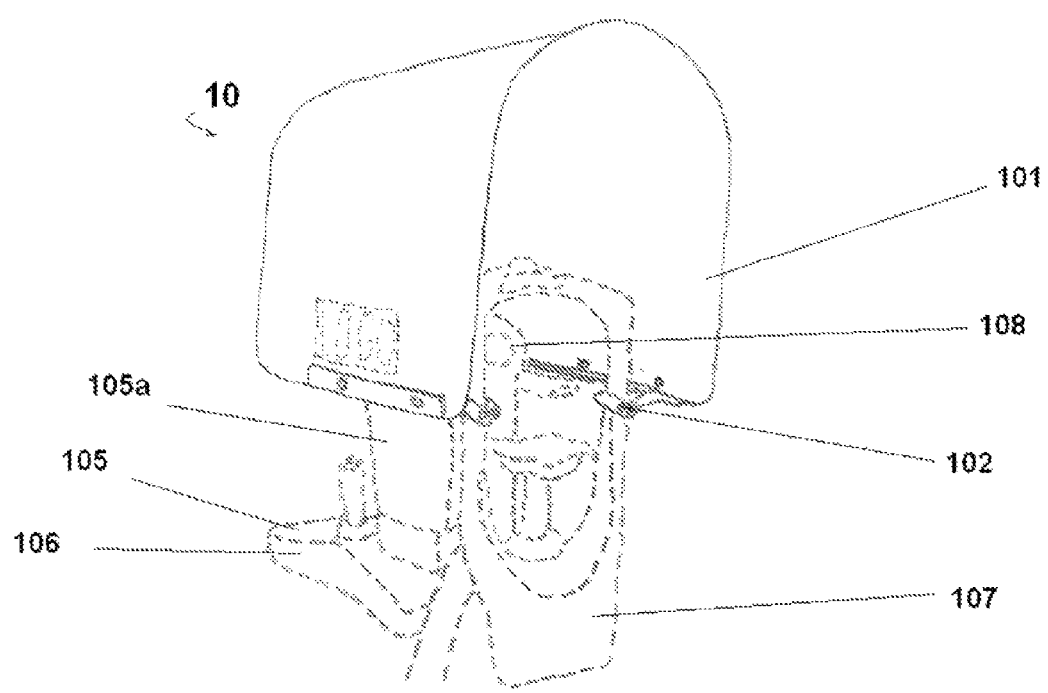
FIG. 4 shows a frontal perspective view of the embodiment in FIG. 3.

FIG. 4 shows another embodiment of the parabolic hood 10 mounted on to an ophthalmic instrument 105. In this view, a light collecting device 108 is illustrated, including a more detailed view of the chin/head rest 107.

Figure 5:
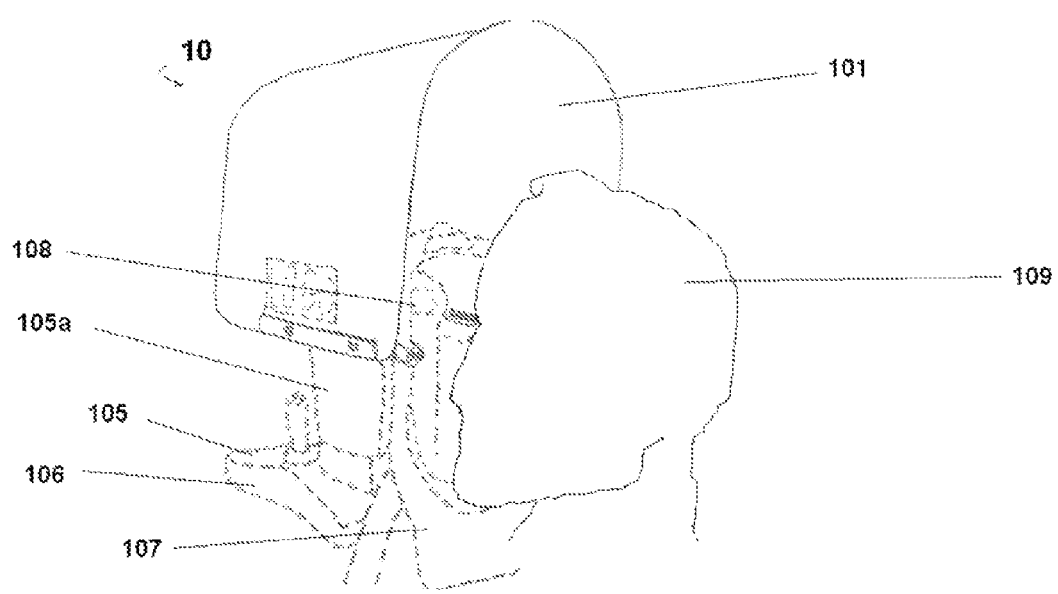
FIG. 5 shows a view of the embodiment of FIG. 4 with a subject under examination using the parabolic hood anchored to an ophthalmic instrument.

FIG. 5 shows the same perspective view of the system where a subject's head 109 is positioned on the chin/head rest 107, such that the subject's eyes are aligned with the light collecting/projecting 108 device of the instrument 105. As will be appreciated in view of the figures, once correctly positioned, the hood 10/1i may cover the head of the subject 109 approximately mid-cranially, thus shielding the subject's eyes from exposure to extraneous light.

It will be appreciated that various of the above-disclosed and other features and functions, or alternatives thereof, may be desirably combined into many other different systems or applications. Also various presently unforeseen or unanticipated alternatives, modifications, variations or improvements therein may be subsequently made by those skilled in the art, which are also intended to be encompassed by the following claims. Unless specifically recited in a claim, steps or components of claims should not be implied or imported from the specification or any other claims as to any particular order, number, position, size, shape, angle, color or material.

All references cited herein are herein incorporated by reference in entirety.

We claim herein:

1. An ophthalmic system comprising:
   an ophthalmic instrument comprising a housing, a headrest and chinrest attached to said housing, and a light collecting device; and
   a substantially rectangular opaque parabolic hood anchored to one or more outer surfaces of said instrument, wherein the apex of said parabolic hood is above the housing of the instrument and the base of said parabolic hood runs parallel to the horizontal axis of the housing, wherein the parabolic hood comprises one or more thin sheets, and wherein the parabolic hood is configured to cover at least: (i) the light collecting device of the instrument; and (ii) the front of the head of a subject substantially mid-cranially when the front of the head of the subject is proximal to said light collecting device.

2. The optical system of claim 1, wherein the parabolic hood comprises at least two substantially rectangular deflectable plates attached to an inner surface of said parabolic hood, wherein the top of the deflectable plates is proximal to the beginning of the inner curvature of the arc of the parabolic hood and the bottom of the deflectable plates is parallel to the base of the parabolic hood.

3. The optical system of claim 2, wherein the deflectable plates are configured to substantially oppose each other.

4. The optical system of claim 3, wherein the deflectable plates are attached to the inner surface of the hood through hinges attached to the base of the parabolic hood distal to the parabolic apex.

5. The optical system of claim 2, wherein the deflectable plates deviate 180° relative to the long axis of said base of the parabolic hood.

6. The optical system of claim 1, wherein the one or more thin sheets comprise a material selected from a polymer, metal, composite or combination thereof.

7. The optical system of claim 1, wherein the ophthalmic instrument is selected from a retinal camera, an aberrometer, an ophthalmoscope, an imaging system, a fundus camera, a refraction system, a manual refractor, a reflectometer, a wavefront system, a tomographer, a slit-lamp system, a phoroptor, a perimeter, a keratometer, head-anchored binoculars, a tonometer, an autorefractor, and an optical coherence tomographer.

8. The optical system of claim 1, wherein the parabolic hood is releasably anchored to the one or more surfaces of said ophthalmic instrument.

9. The optical system of claim 8, wherein parabolic hood is releasably anchored by a one or more clamps.

10. The optical system of claim 1, wherein the one or more surfaces are selected from the top, bottom or side surfaces of the housing, the arms of a head rest, the arms of a chin rest or a combination thereof.

11. A substantially rectangular opaque parabolic hood comprising:
   (a) one or more thin sheets comprising a material selected from a polymer, metal, composite or combination thereof; and
   (b) at least two substantially rectangular deflectable plates attached to an inner surface of said parabolic hood, wherein the top of the deflectable plates is proximal to the beginning of the curvature of the arc of the parabolic hood and the bottom of the deflectable plates is parallel to the base of the parabolic hood, wherein said hood does not contain a head or chinrest.

12. The opaque parabolic hood of claim 11, wherein the deflectable plates are configured to substantially oppose each other.

13. The opaque parabolic hood of claim 11, wherein the deflectable plates are attached to the inner surface of the hood through hinges connected to the base of the parabolic hood distal to the parabolic apex.

14. The opaque parabolic hood of claim 11, wherein the deflectable plates deviate 180° relative to the long axis of said base of the parabolic hood.

15. A method of reducing the accommodation response of the pupil during an eye examination using an ophthalmic instrument comprising positioning the head of a subject undergoing examination on a surface of an ophthalmic instrument proximal to a light collecting device of said instrument such that an illumination device contained in said ophthalmic instrument projects light into at least one eye of the subject, wherein the ophthalmic instrument comprises a housing, a headrest and chinrest attached to said housing, and a substantially rectangular opaque parabolic hood anchored to one or more outer surfaces of said instrument, wherein the apex of said parabolic hood is above the light collecting device of the instrument, and wherein said parabolic hood covers the head of the subject substantially mid-cranially, whereby the parabolic hood blocks extraneous light projected above or laterally relative to the head of the subject from entering the at least one eye.

16. The method of claim 15, wherein the parabolic hood comprises at least two substantially rectangular deflectable plates attached to an inner surface of said parabolic hood, wherein the top of the deflectable plates is proximal to the beginning of the curvature of the arc of the parabolic hood and the bottom of the deflectable plates is parallel to the base of the parabolic hood.

17. The method of claim 16, wherein the deflectable plates deviate 180° relative to the long axis of said base of the parabolic hood.

18. The method of claim 16, wherein the plates reduce the depth of focus in the at least one eye.

19. The method of claim 15, wherein the ophthalmic instrument is selected from a retinal camera, an aberrometer, an ophthalmoscope, an imaging system, a fundus camera, a refraction system, a manual refractor, a reflectometer, a wavefront system, a tomographer, a slit-lamp system, a phoroptor, a perimeter, a keratometer, head-anchored binoculars, a tonometer, an autorefractor, and an optical coherence tomographer.

20. The method of claim 15, wherein the one or more surfaces are selected from the arms of a head rest, the arms of a chin rest or a combination thereof.

* * * * *